(12) United States Patent
Morishima

(10) Patent No.: US 10,634,125 B2
(45) Date of Patent: Apr. 28, 2020

(54) VARIABLE-STIFFNESS ACTUATOR

(71) Applicant: OLYMPUS CORPORATION, Tokyo (JP)

(72) Inventor: Tetsuya Morishima, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 54 days.

(21) Appl. No.: 15/822,587

(22) Filed: Nov. 27, 2017

(65) Prior Publication Data

US 2018/0080437 A1    Mar. 22, 2018

Related U.S. Application Data

(63) Continuation of application No. PCT/JP2015/065211, filed on May 27, 2015.

(51) Int. Cl.
    *F03G 7/06*      (2006.01)
    *A61B 1/00*      (2006.01)
    *A61B 1/005*      (2006.01)

(52) U.S. Cl.
    CPC .............. *F03G 7/065* (2013.01); *A61B 1/00* (2013.01); *A61B 1/0053* (2013.01); *A61B 1/0057* (2013.01); *A61B 1/0058* (2013.01)

(58) Field of Classification Search
    CPC .......... A61B 1/0058; A61B 1/04; A61B 1/06; A61B 1/00039; A61B 1/00048; A61B 1/0005; A61B 1/00071; A61B 1/042; A61B 1/005; F03G 7/065; F03G 600/109; F03G 600/114; F03G 600/115; F03G 600/178; F03G 600/143; F03G 600/146
    USPC .............................. 60/527–529; 310/306–307
    See application file for complete search history.

(56) References Cited

U.S. PATENT DOCUMENTS

2015/0282693 A1* 10/2015 Hakkens ............... A61L 29/126
    604/95.05

FOREIGN PATENT DOCUMENTS

| JP | S58101601 U | 7/1983 |
| JP | H06114003 A | 4/1994 |
| JP | H07-072927 A | 3/1995 |
| JP | 3122673 B2 | 1/2001 |

(Continued)

OTHER PUBLICATIONS

Machine translation of Aramaki (JP 07072927) Mar. 17, 1995.*

(Continued)

*Primary Examiner* — Mark A Laurenzi
*Assistant Examiner* — Mickey H France
(74) *Attorney, Agent, or Firm* — Scully, Scott, Murphy & Presser, P.C.

(57) ABSTRACT

A variable-stiffness actuator, installed in a flexible member and capable of providing different stiffnesses for the flexible member, includes a shape-memory member that can transit in phase between first and second phases and an inducing member that causes phase transition between the first and second phases into the shape-memory member. The shape-memory member takes, in the first stare, a flexible state in which it is easily deformable by an external force, so as to provide lower stiffness for the flexible member, and, in the second stare, a rigid state in which it tends to take a memorized shape against an external force, so as to provide higher stiffness for the flexible member. The actuator further includes a stiffness calculator that calculates the stiffness of the actuator.

5 Claims, 9 Drawing Sheets

(56) References Cited

FOREIGN PATENT DOCUMENTS

JP          3142928 B2    3/2001
JP     2005279118 A   10/2005

OTHER PUBLICATIONS

International Search Report dated Aug. 18, 2015 issued in PCT/JP2015/065211.
English translation of International Preliminary Report on Patentability dated Dec. 7, 2017 together with the Written Opinion received in related International Application No. PCT/JP2015/065211.
Japanese Office Action dated Sep. 18, 2018 in Japanese Patent Application No. 2017-520149.

* cited by examiner

VARIABLE-STIFFNESS ACTUATOR

CROSS REFERENCE TO RELATED APPLICATIONS

This application is a Continuation Application of PCT Application No. PCT/JP2015/065211, filed May 27, 2015, the entire contents of which are incorporated herein by reference.

1. FIELD OF THE INVENTION

The present invention relates to a variable-stiffness actuator for varying the stiffness of a flexible member.

2. DESCRIPTION OF THE RELATED ART

Japanese Patent No. 3122673 discloses an endoscope in which the stiffness of a flexible portion of an insertion section is allowed to be varied. In this endoscope, a flexible member (e.g. a coil pipe) has both ends fixed at predetermined positions in the endoscope, and a flexibility adjustment member (e.g. flexibility adjustment wire inserted through a coil pipe) is fixed to the flexible member through a separator. The flexible member and the flexibility adjustment member extend to an operation section along the flexible portion and extend almost all over the flexible portion. The flexible member is compressed and stiffened by pulling the flexibility adjustment member, thereby; the stiffness of the flexible portion is varied.

Japanese Patent No. 3142928 discloses a variable-stiffness apparatus for flexible tubes using a shape-memory alloy. The variable-stiffness apparatus includes a coil provided in a flexible tube, an electrical insulative tube provided inside the coil, a shape-memory alloyed wire located in the electrical insulative tube to extend in its axial direction, and an energization heating means to energize the shape-memory alloyed wire.

The shape-memory alloyed wire has the properties of elongating at a low temperature and contracting at a high temperature. The shape-memory alloyed wire extends out through fixed portions at both ends of the coil, and caulking members are fixed to the both ends. The shape-memory alloyed wire is arranged so that it loosens at a low temperature and it tightens up with the caulking members being engaged with the fixed portions at a high temperature.

The shape-memory alloyed wire contracts to stiffen the coil at a high temperature at which it is energized by the energization heating means. On the other hand, the shape-memory alloyed wire elongates to soften the coil at a low temperature at which it is not energized.

BRIEF SUMMARY OF THE INVENTION

A variable-stiffness actuator, installed in a flexible member and capable of providing different stiffnesses for the flexible member, includes a shape-memory member that can transit in phase between a first phase and a second phase and an inducing member that causes phase transition between the first phase and the second phase into the shape-memory member. The shape-memory member takes a flexible state in which it is easily deformable by an external force when it is in the first stare, so as to provide lower stiffness for the flexible member. The shape-memory member takes a rigid state in which it tends to take a memorized shape memorized beforehand against an external force when it is in the second stare, so as to provide higher stiffness for the flexible member. The variable-stiffness actuator further includes a stiffness calculator that calculates the stiffness of the variable-stiffness actuator.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

First Embodiment

[Constitution]

Figure 1:
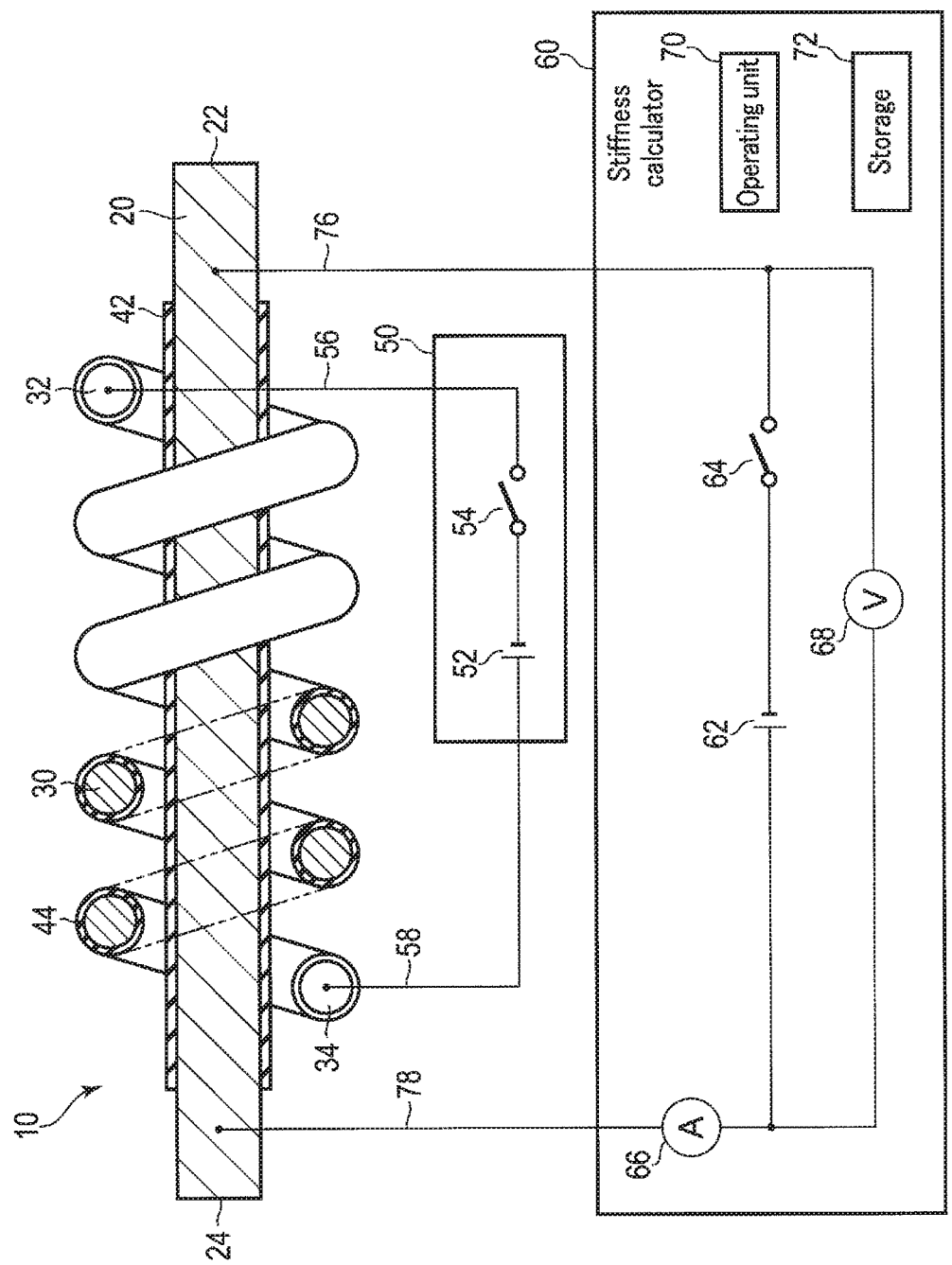
FIG. 1 shows a variable-stiffness actuator according to a first embodiment.

FIG. 1 shows a variable-stiffness actuator according to an embodiment. As shown in FIG. 1, a variable-stiffness actuator 10, which has a function of providing different stiffnesses for a flexible member by taking different stiffness states, includes a shape-memory member 20 that can transit in phase between a first phase and a second phase and an inducing member 30 that causes phase transition between the first phase and the second phase into the shape-memory member 20. The shape-memory member 20 is arranged in the flexible member with at least one free end.

The shape-memory member 20 takes a flexible state in which it is easily deformable by an external force, or it exhibits a low elastic modulus, when it is in the first stare, so as to provide lower stiffness for the flexible member. The shape-memory member 20 takes a rigid state in which it tends to take a memorized shape memorized beforehand against an external force, or it exhibits a high elastic modulus, when it is in the second stare, so as to provide higher stiffness for the flexible member. The memorized shape may be, but not limited to, a linear shape.

Herein, the external force means force that can cause the shape-memory member 20 to be deformed, and gravity is considered to be part of the external force.

The inducing member 30 has performance of generating heat. The shape-memory member 20 has properties of transiting in phase from the first phase to the second phase in response to the heating of the inducing member 30.

The shape-memory member 20 may be constituted from, e.g. a shape-memory alloy. The shape-memory alloy may be alloy including, but not limited to, e.g. NiTi. The shape-memory member 20 may also be constituted from another material, but not limited to, such as shape-memory polymer, shape-memory gel and shape-memory ceramics.

The shape-memory alloy that constitutes the shape-memory member 20 may be, for example, something that transits in phase between a martensitic phase and an austenitic phase. In the martensitic phase, the shape-memory alloy is plastically deformed relatively easily by an external force. In other words, the shape-memory alloy exhibits a low elastic modulus in the martensitic phase. In the austenitic phase, the shape-memory alloy is not easily deformed by an external force. Even though the shape-memory alloy is deformed by a greater external force, it exhibits superelasticity and returns to its memorized shape when the greater external force is lost. In other words, the shape-memory alloy exhibits a high elastic modulus in the austenitic phase.

The inducing member 30 may be constituted by, e.g. a heater. In other words, the inducing member 30 may have properties of generating heat upon receipt of current flowing therethrough. The inducing member 30 may be a heating wire, or a conductive member with high electrical resistance. The inducing member 30 has only to have performance of generating heat and may be constituted by, but not limited to the heater, an image pickup element, a light guide, another element or member, etc. The inducing member 30 may also be constituted by a structure that generates heat by a chemical reaction.

The shape-memory member 20 may be constituted from a conductive material. For example, an insulation film 42 is provided on the circumferential side surface of the shape-memory member 20. The insulation film 24 serves to prevent a short circuit from occurring between the shape-memory member 20 and the inducing member 30. The insulation film 24 is provided to cover at least a portion facing the inducing member 30. FIG. 1 illustrates a configuration in which the insulation film 24 is provided on the shape-memory member 20 with partly covering the circumferential side surface, but not limited to that, the insulation film 24 may be provided on the shape-memory member 20 with covering all of the circumferential side surface or so as to cover entirely the shape-memory member 20.

The inducing member 30 may be constituted from a conductive material. For example, an insulation film 44 is provided around the inducing member 30. The insulation film 34 serves to prevent a short circuit from occurring between the shape-memory member 20 and the inducing member 30 and a short circuit from occurring between adjacent portions of the inducing member 30.

The variable-stiffness actuator 10 includes an insulation member to prevent a short circuit from occurring between the shape-memory member 20 and the inducing member 30. The insulation film 42 and the insulation film 44 correspond to the insulation member. If the insulation film 44 has a reliable short-circuit prevention function, the insulation film 42 may be omitted.

The shape-memory member 20 has a first end 22 and a second end 24, and the inducing member 30 has a first end 32 located close to the first end 22 of the shape-memory member 20 and a second end 34 located close to the second end 24 of the shape-memory member 20. Both the shape-memory member 20 and the inducing member 30 are conductive. The first end 32 of the inducing member 30 is electrically connected to a controller 50 through a wire 56. The second end 34 of the inducing member 30 is electrically connected to the controller 50 through a conductive member 58.

The controller 50 is to control the stiffness of the shape-memory member 20 and so includes a power source 52 and a switch 54. The controller 50 supplies current to the inducing member 30 in response to the operation of turning on or closing the switch 54, and stops supplying the current to the inducing member 30 in response to the operation of turning off or opening the switch 54. The inducing member 30 generates heat in response to the supply of current.

Near the first end 22, the shape-memory member 20 is electrically connected to a stiffness calculator 60 through a wire 76. Near the second end 24, the shape-memory member 20 is electrically connected to the stiffness calculator 60 through a wire 78.

The stiffness calculator 60 is to calculate the stiffness of the variable-stiffness actuator 10 and includes a power source 62 and a switch 64 connected in series. The complex of the power source 62 and the switch 64 is electrically connected to wire 76 on the switch side and is electrically connected to wire 78 on the power source side.

The stiffness calculator 60 further includes a current detector 66 to detect current flowing through the power source 62 and the switch 64, and a voltage detector 68 to detect voltage applied across the complex of the power source 62 and the switch 64.

The stiffness calculator 60 further includes an operating unit 70 to calculate the stiffness of the variable-stiffness actuator 10, based on the information obtained by the current detector 66 and the information obtained by the voltage detector 68, and a storage 72 to store a relationship between the temperature and stiffness of the shape-memory member 20 and a temperature history of the shape-memory member 20. The operating unit 70 preferably calculates the variable-stiffness actuator 10 in view of the temperature history of the shape-memory member 20, in addition to the information obtained by the current detector 66 and the information obtained by the voltage detector 68.

The shape-memory member 20 may be shaped like a wire. The inducing member 30 is arranged close to the shape-memory member 20. The inducing member 30 may be shaped like a coil, and the shape-memory member 20 may extend through the inside of the coil-shaped inducing member 30. With this arrangement, the heat generated from the inducing member 30 is transmitted to the shape-memory member 20 with efficiency.

[Description of Operation of Variable-Stiffness Actuator Alone]

Hereinafter, an operation of the foregoing variable-stiffness actuator will be described with reference to FIGS. 2-7. For convenience of description, it is assumed that an end of the shape-memory member 20 is fixed. It is also assumed that the memorized shape of the shape-memory member 20 is a linear shape. In FIGS. 2-7, the shape-memory member 20 in the flexible state is indicated by upper left hatching and the shape-memory member 20 in the rigid state is indicated by upper right hatching.

Figure 2:
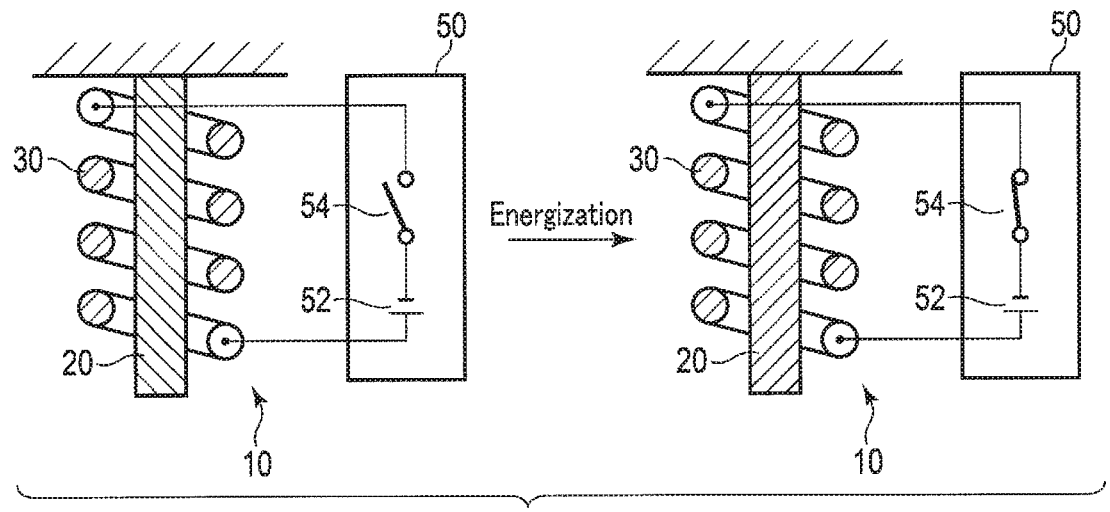
FIG. 2 is an illustration for explaining an operation of a variable-stiffness actuator, showing how the stiffness state of a shape-memory member is varied by switching a switch of a drive circuit.

FIG. 2 shows how the stiffness state of the shape-memory member 20 is varied by switching the switch 54 of the controller 50.

On the left side of FIG. 2, the switch 54 of the controller 50 is in an off state or opened, and the shape-memory member 20 is in the first phase that is the flexible state with a low elastic modulus.

When the switch 54 of the controller 50 is switched to an on state or closed as shown in the right side of FIG. 2, current flows through the inducing member 30, the inducing member 30 generating heat. Accordingly, the shape-memory member 20 transits to the second phase that is the rigid state with a high elastic modulus.

Figure 3:
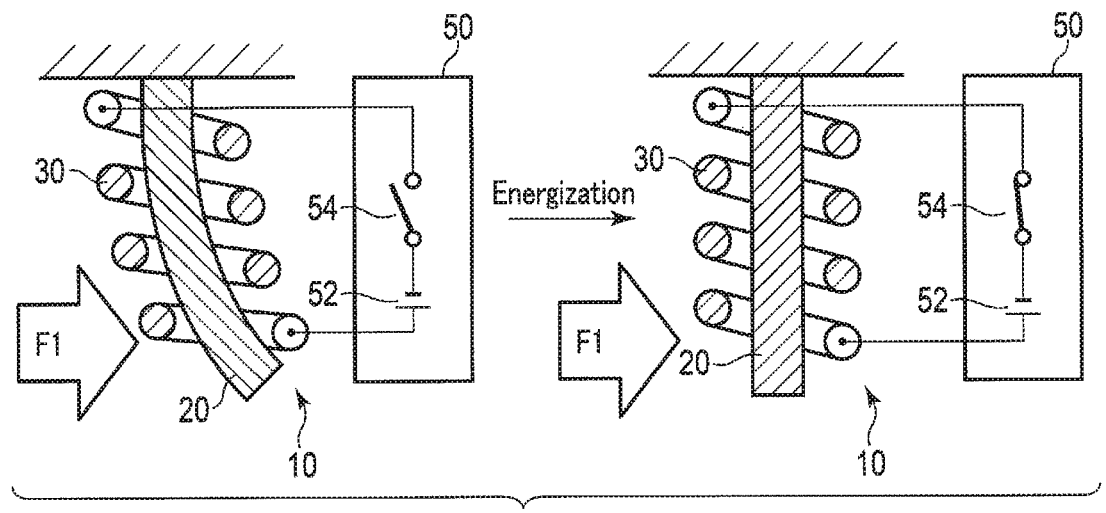
FIG. 3 is an illustration for explaining an operation of a variable-stiffness actuator, showing how the stiffness state of a shape-memory member is varied by switching a switch of a drive circuit in a situation where an external force is exerted on the vicinity of a free end of the shape-memory member in a direction perpendicular to the central axis of the shape-memory member.

FIG. 3 shows how the stiffness state of the shape-memory member 20 is varied by switching the switch 54 of the controller 50 in a situation where an external force F1 is exerted on the vicinity of the free end of the shape-memory member 20 in a direction perpendicular to the central axis of the shape-memory member 20. The external force F1 is smaller than a restoring force when the shape-memory member 20 will return to its memorized shape.

On the left side of FIG. 3, the switch 54 of the controller 50 is in the off state, and the shape-memory member 20 is in the first phase that is the flexible state. In the first phase, the shape-memory member 20 is in a state in which it is easily deformed by the external force F1. The shape-memory member 20 is bent by the external force F1.

When the switch 54 of the controller 50 is switched to the on state as shown in the right side of FIG. 3, the inducing member 30 generates heat and the shape-memory member 20 transits to the second phase that is the rigid state. In the second phase, the shape-memory member 20 tends to take its memorized shape. In other words, if the shape of the shape-memory member 20 differs from the memorized shape, the shape-memory member 20 will return to the memorized shape. Since the external force F1 is smaller than the restoring force of the shape-memory member 20, the shape-memory member 20 returns to the memorized shape or linear shape against the external force F1.

Figure 4:
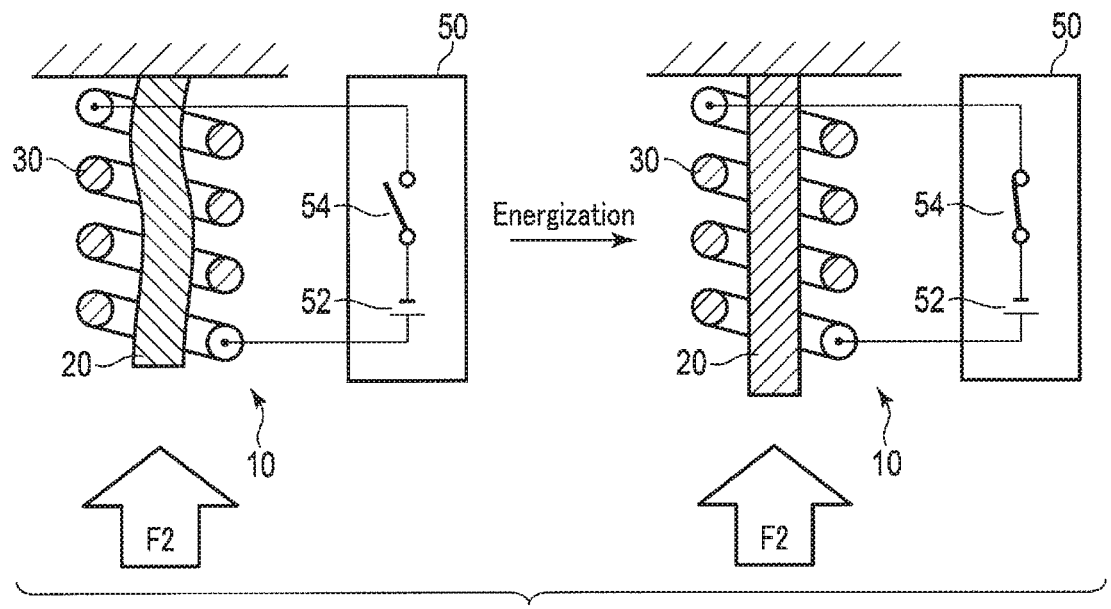
FIG. 4 is an illustration for explaining an operation of a variable-stiffness actuator, showing how the stiffness state of a shape-memory member is varied by switching a switch of a drive circuit in a situation where an external force is exerted on a free end of the shape-memory member in a direction parallel to the central axis of the shape-memory member.

FIG. 4 shows how the stiffness state of the shape-memory member 20 is varied by switching the switch 54 of the controller 50 in a situation where an external force F2 is exerted on the free end of the shape-memory member 20 in a direction parallel to the central axis of the shape-memory member 20. The external force F2 is smaller than the restoring force when the shape-memory member 20 will return to its memorized shape.

On the left side of FIG. 4, the switch 54 of the controller 50 is in the off state, and the shape-memory member 20 is in the first phase that is the flexible state. In the first phase, the shape-memory member 20 is in a state in which it is easily deformed by the external force F2. The shape-memory member 20 is compressed by the external force F2. In other words, the shape-memory member 20 is reduced in its length or its dimension along the central axis with bet.

When the switch 54 of the controller 50 is switched to the on state as shown in the right side of FIG. 4, the inducing member 30 generates heat and the shape-memory member 20 transits to the second phase that is the rigid state. In the second phase, the shape-memory member 20 tends to take its memorized shape. Since the external force F2 is smaller than the restoring force of the shape-memory member 20, the shape-memory member 20 returns to the memorized shape or linear shape against the external force F2.

Figure 5:
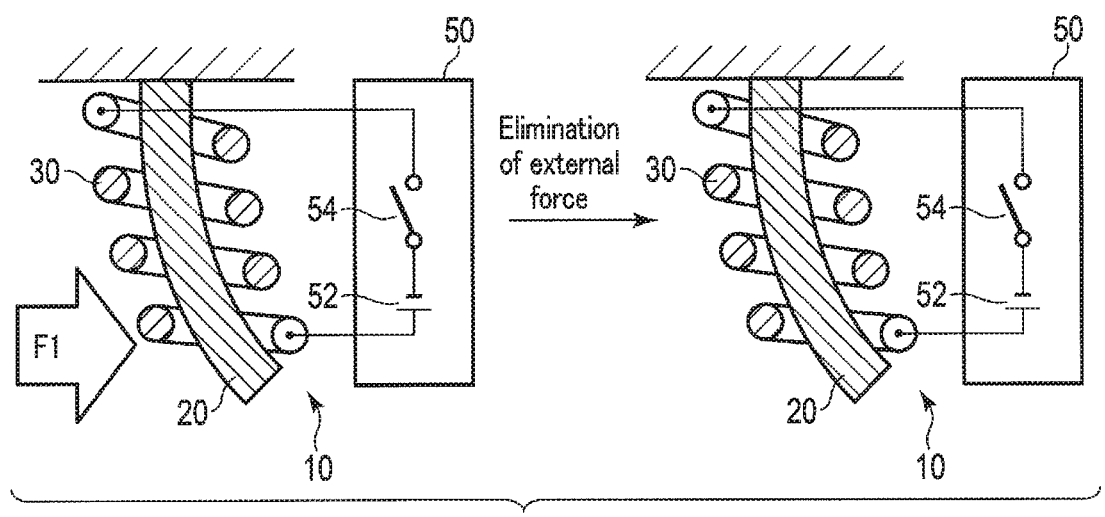
FIG. 5 is an illustration for explaining an operation of a variable-stiffness actuator, showing how the presence and absence of an external force are switched in a situation where a switch of a drive circuit is in an off state and a shape-memory member is in a flexible state.

FIG. 5 shows how the presence and absence of an external force are switched in a situation where the switch 54 of the controller 50 is in the off state and the shape-memory member 20 is in the flexible state. In the first phase, the shape-memory member 20 is in a state in which it is easily deformed by the external force.

On the left side of FIG. 5, the external force F1 is exerted on the vicinity of the free end of the shape-memory member 20 in a direction perpendicular to the central axis of the shape-memory member 20. The shape-memory member 20 is bent by the external force F1.

On the right side of FIG. 5, the external force F1 that has been so far exerted on the shape-memory member 20 is eliminated. The shape-memory member 20 remains bent after the external force F1 is eliminated.

Figure 6:
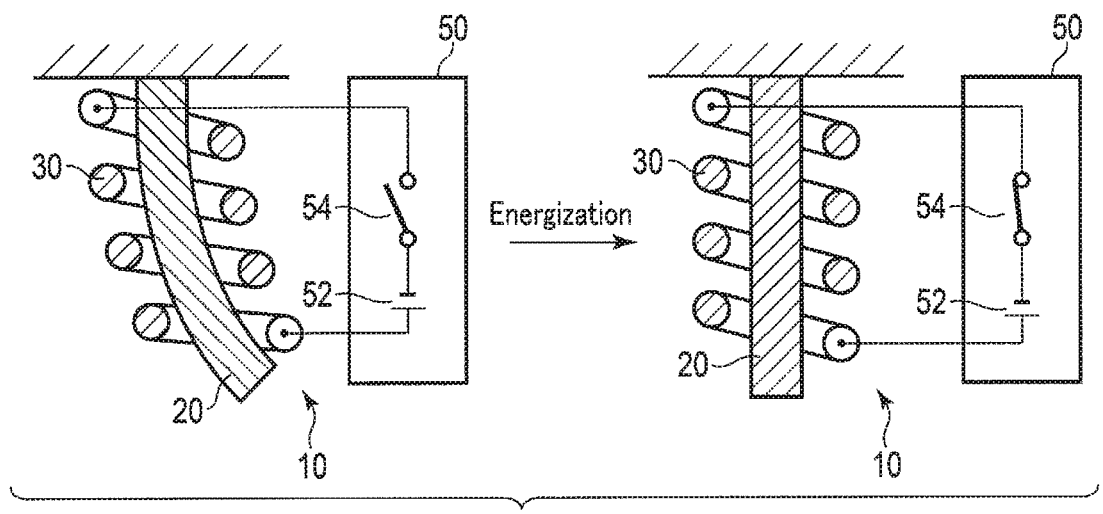
FIG. 6 is an illustration for explaining an operation of a variable-stiffness actuator, showing how the stiffness state of a bent shape-memory member is varied from a flexible state to a rigid state by switching a switch of a drive circuit.

FIG. 6 shows how the stiffness state of the bent shape-memory member 20 is varied from the flexible state to the rigid state by switching the switch 54 of the controller 50.

The left side of FIG. 6 shows the same state as that of the right side of FIG. 5 and, in other words, the shape-memory member 20 is bent by the external force F1, and then remains bent after the external force F1 is eliminated.

When the switch 54 of the controller 50 is switched to the on state as shown in the right side of FIG. 6, the inducing member 30 generates heat and the shape-memory member 20 transits to the second phase that is the rigid state. In the second phase, since the shape-memory member 20 tends to take its memorized shape, the shape-memory member 20 returns to the memorized shape or linear shape.

Figure 7:
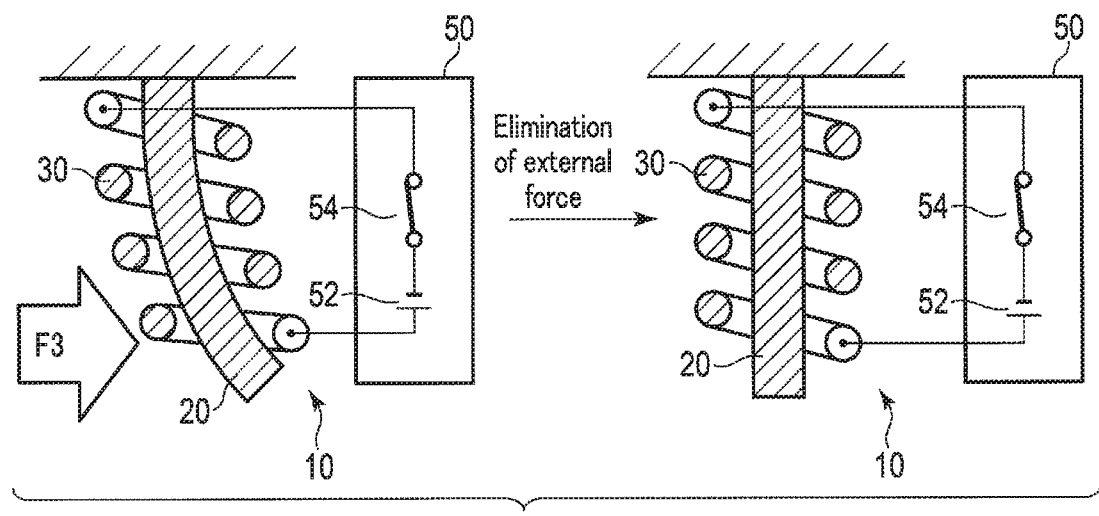
FIG. 7 is an illustration for explaining an operation of a variable-stiffness actuator, showing how the presence and absence of an external force are switched in a situation where a switch of a drive circuit is in an on state and a shape-memory member is in a rigid state.

FIG. 7 shows how the presence and absence of an external force are switched in a situation where the switch 54 of the controller 50 is in the on state and the shape-memory member 20 is in the second phase that is the rigid state. In the second phase, the shape-memory member 20 tends to take its memorized shape.

The left side of FIG. 7 shows how an external force F3 is exerted on the vicinity of the free end of the shape-memory member 20 in a direction perpendicular to the central axis of the shape-memory member 20. The external force F3 is greater than a restoring force when the shape-memory member 20 will return to its memorized shape. Though the shape-memory member 20 will return to its memorized shape against the external force F3, since the external force F3 is greater than the restoring force of the shape-memory member 20, the shape-memory member 20 is bent by the external force F3.

On the right side of FIG. 7, the external force F3 that has been so far exerted on the shape-memory member 20 is eliminated. Since the external force F3 that is greater than the restoring force of the shape-memory member 20 is eliminated, the shape-memory member 20 has returned to its memorized shape or linear shape.

[Description of Operation and Attachment Method of Variable-Stiffness Actuator]

The foregoing variable-stiffness actuator 10 is installed in a flexible member without restricting both ends of the shape-memory member 20. For example, the variable-stiffness actuator 10 is placed in a limited space of the flexible member with a small clearance so that an end or both ends of the shape-memory member 20 are a free end or free ends.

Herein, the limited space means space capable of exactly containing the variable-stiffness actuator 10. Thus, even though one of the variable-stiffness actuator 10 and the flexible member is slightly deformed, it can contact the other and give an external force.

For example, the flexible member may be a tube having an inner diameter that is slightly larger than the outer diameter of the variable-stiffness actuator 10, and the variable-stiffness actuator 10 may be placed inside the tube. Without limiting to this, the flexible member has only to have space that is slightly larger than the variable-stiffness actuator 10.

When the shape-memory member 20 is in the first phase, the variable-stiffness actuator 10 provides lower stiffness for the flexible member and is easily deformed by an external force exerted on the flexible member, or force capable of deforming the shape-memory member 20.

When the shape-memory member 20 is in the second phase, the variable-stiffness actuator 10 provides higher stiffness for the flexible member and tends to return to its memorized shape against an external force exerted on the flexible member, or force capable of deforming the shape-memory member 20.

For example, the phase of the shape-memory member 20 is switched between the first and second phases by the controller 50 switches, so that the stiffness of the flexible member is switched.

In addition to the switching of stiffness, in a situation where an external force is exerted on the flexible member, the variable-stiffness actuator 10 also serves as a bidirectional actuator that switches the shape of the flexible member. In another situation where no external force is exerted on the flexible member but the flexible member is deformed in the first phase before the phase of the shape-memory member 20 is switched to the second phase, it also serves as a unidirectional actuator that returns the shape of the flexible member to the original.

[Relationship Between Temperature and Stiffness of Shape-Memory Member 20]

Figure 8:
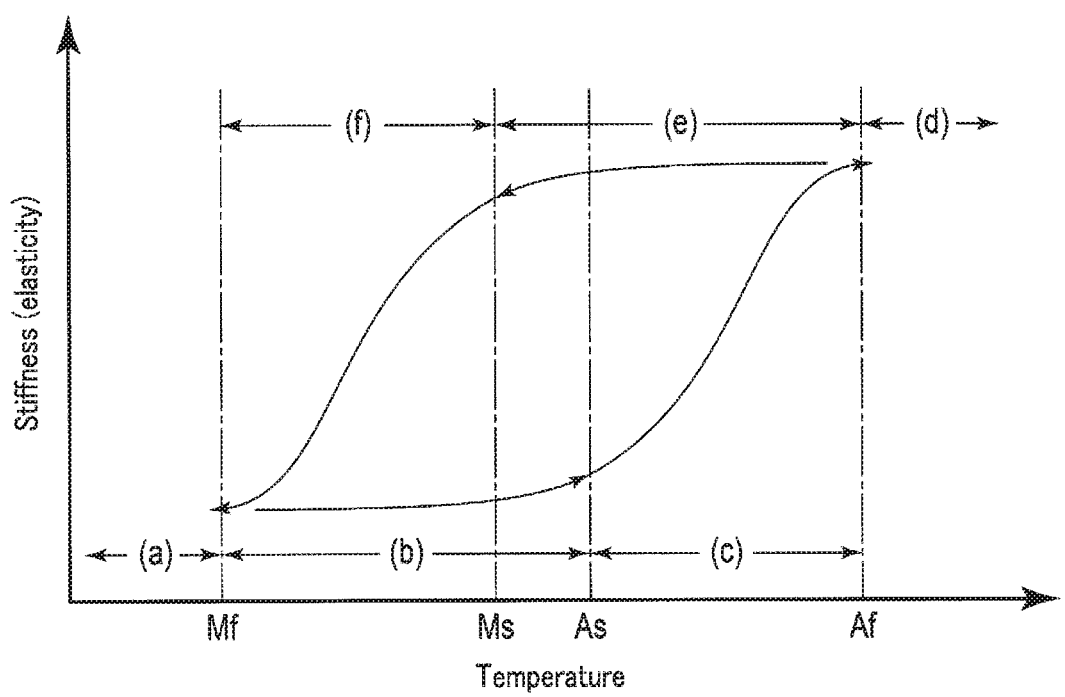
FIG. 8 shows a relationship between the temperature and stiffness in a variable-stiffness actuator.

FIG. 8 shows a relationship between the temperature and stiffness of the shape-memory member 20 of the variable-stiffness actuator 10. The relationship between the temperature and stiffness of the shape-memory member 20 vary, depending upon the shape-memory member 20 and inducing member 30 that are in use. The relationship between the temperature and stiffness of the shape-memory member 20 is acquired beforehand and stored in the storage 72. As can be understood from FIG. 8, the relationship between the temperature and stiffness of the shape-memory member 20 has a hysteresis.

In FIG. 8, (a) indicates a temperature range that is less than Mf (martensite finish), and the shape-memory member 20 has the lowest stiffness in this temperature range.

(d) indicates a temperature range that is more than Af (austenite finish), and the shape-memory member 20 has the highest stiffness in this temperature range.

In these two temperature ranges, the stiffness of the shape-memory member 20 can be calculated directly from the temperature of the shape-memory member 20.

However, since the relationship between the temperature and stiffness of the shape-memory member 20 has the hysteresis, the stiffness of the shape-memory member 20 has to be calculated in consideration of the temperature history, in the temperature ranges between the above-mentioned two temperature ranges (a) and (d). A description will be given of this point.

(b) indicates a temperature range that is more than Mf and less than As (austenite start), and that starts from Mf to rise and not to exceed As. In this temperature range, the stiffness of the shape-memory member 20 is almost the same as the stiffness exhibited in temperature range (a).

(c) indicates a temperature range that is more than As and less than Af, and that starts from As to rise and not to exceed Af. In this temperature range, the stiffness of the shape-memory member 20 increases as the temperature increases from As to Af.

(e) indicates a temperature range that is less than Af and more than Ms (martensite start), and that starts from Af to lower and not to fall below Ms. In this temperature range, the stiffness of the shape-memory member 20 is almost the same as the stiffness exhibited in temperature range (d).

(f) indicates a temperature range that is less than Ms and more than Mf, and that starts from Ms to lower and not to fall below Mf. In this temperature range, the stiffness of the shape-memory member 20 decreases as the temperature decreases from Ms to Mf.

That is, the stiffness of the shape-memory member 20 cannot be unambiguously determined by the temperature alone. In other words, the stiffness of the shape-memory member 20 cannot be calculated from the temperature alone. In order to calculate the stiffness of the shape-memory member 20, the temperature history of the shape-memory member 20 has to be taken into consideration in addition to the current temperature of the shape-memory member 20. The temperature history of the shape-memory member 20 may be information indicating how the temperature of the shape-memory member 20 is at each point of time, in other words, paired information indicative of each point of time and the related temperature. Such information is stored in the storage 72 during the operation of the variable-stiffness actuator 10.

[Calculation of Stiffness of Stiffness-Variable Actuator 10]

The resistance of a conductor increases as the temperature of the resistance increases. By utilization of this principle, the present embodiment applies voltage across a shape-memory alloy, calculates a resistance value from the current flowing through the shape-memory alloy, and translates the resistance value to the temperature. In many cases, the temperature is hard to be calculated based on the resistance value of the shape-memory alloy. The reason is that the shape-memory alloy changes its shape in response to the temperature, and the cross sectional area and the length of the shape-memory alloy change. In the present variable-stiffness actuator 10, the stiffness change of the shape-memory member 20 is used, so that the resistance change attributable to the shape change is so small that the temperature can be translated from the resistance value.

To supplement the description, in many cases, a general shape-memory alloy actuator utilizes a shape change occurring in the longitudinal direction. Accordingly, the cross sectional area and length change greatly, so that the resistance value inevitably undergoes a great change. In the present variable-stiffness actuator 10, however, since the shape change occurs in the radial direction, the cross sectional area and the length do not change greatly, so that the resistance value does not change greatly. As should be clear from the above, in the present variable-stiffness actuator 10, the temperature can be calculated from the resistance value and the stiffness can be calculated from the temperature with higher accuracy than the above-mentioned general cases.

The stiffness calculator 60 applies voltage across the shape-memory member 20, causing current to flow through the shape-memory member 20. The current detector 66 measures the value of the current flowing through the shape-memory member 20. The voltage detector 68 measures the value of the voltage applied to the shape-memory member 20. The operating unit 70 calculates the resistance value of the shape-memory member 20, based on the current value obtained by the current detector 66 and the voltage value obtained by the voltage detector 68. The operating unit 70 also calculates the temperature of the shape-memory member 20, based on the calculated resistance value. The storage 72 stores the calculated temperature of the shape-memory member 20 together with the related point of time.

The operating unit 70 further calculates the stiffness of the variable-stiffness actuator 10, based on the calculated temperature of the shape-memory member 20 and the temperature history of the shape-memory member 20 stored in the storage 72. To be more specific, the operating unit 70 determines whether the temperature rises to the present temperature or lowers to the present temperature, based on the temperature history of the shape-memory member 20. With the result of determination taken into account, the operating unit 70 calculates the stiffness of the variable-stiffness actuator 10, based on the relationship between the temperature and stiffness of the shape-memory member 20 stored in the storage 72 and the calculated temperature of the shape-memory member 20.

Second Embodiment

Figure 9:
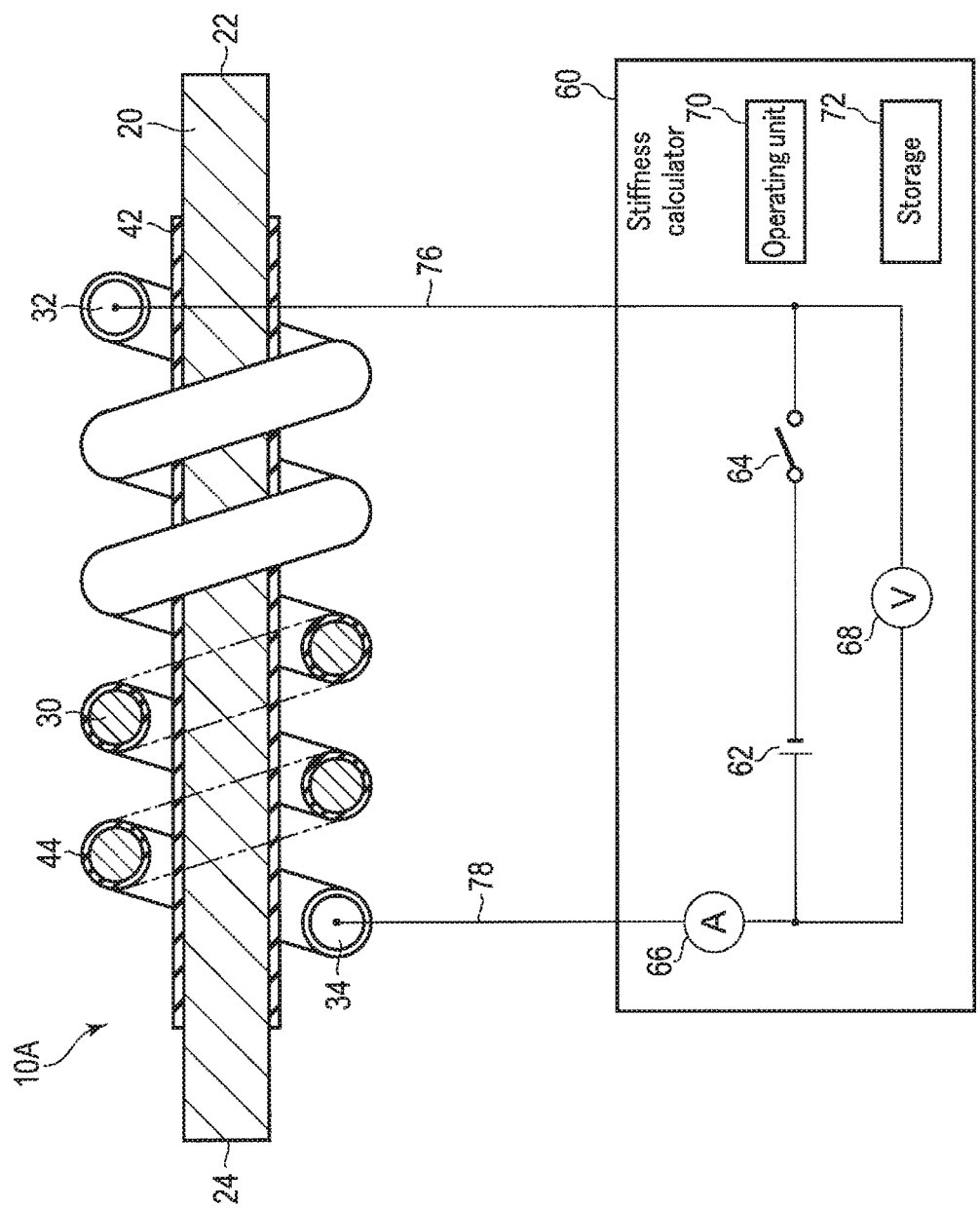
FIG. 9 shows a variable-stiffness actuator according to a second embodiment.

FIG. 9 shows a variable-stiffness actuator according to a second embodiment. In FIG. 9, the members denoted by the same reference numerals as used in FIG. 1 are members similar to those of FIG. 1, and a detailed description of such members will be omitted. Hereinafter, a description will be given mainly of the differences. In other words, the points that will not be mentioned below are similar to those of the aforesaid first embodiment.

In the variable-stiffness actuator 10A of the present embodiment, in comparison with the variable-stiffness actuator 10 of the first embodiment, the controller 50 is omitted. Instead, the first end 32 of the inducing member 30 is electrically connected to the wire 76 connected to the stiffness calculator 60, and the second end 34 of the inducing member 30 is electrically connected to the wire 78 connected to the stiffness calculator 60. That is, in the present embodiment, the stiffness calculator 60 also has the same function as the controller 50 of the first embodiment.

In the present embodiment, the storage 72 stores the relationship between the temperature of the inducing member 30 and the stiffness of the shape-memory member 20 beforehand, in place of the relationship between the temperature and stiffness of the shape-memory member 20 in the first embodiment. The inducing member 30 is conductive, but the shape-memory member 20 need not be necessarily conductive and may be non-conductive.

The stiffness calculator 60 applies voltage across the inducing member 30, causing current to flow through the inducing member 30. The current detector 66 measures the value of the current flowing through the inducing member 30. The voltage detector 68 measures the value of the voltage applied to the inducing member 30. The operating unit 70 calculates the resistance value of the inducing member 30, based on the current value obtained by the current detector 66 and the voltage value obtained by the voltage detector 68. The operating unit 70 also calculates the temperature of the inducing member 30, based on the calculated resistance value. The storage 72 stores the calculated temperature of the inducing member 30 together with the related point of time.

The operating unit 70 further calculates the stiffness of the variable-stiffness actuator 10A, based on the calculated temperature of the inducing member 30 and the temperature history of the inducing member 30 stored in the storage 72. To be more specific, the operating unit 70 determines whether the temperature rises to the present temperature or lowers to the present temperature, based on the temperature history of the inducing member 30. With the result of determination taken into account, the operating unit 70 calculates the stiffness of the variable-stiffness actuator 10A, based on the relationship between the temperature of the inducing member 30 and the stiffness of the shape-memory member 20, which is stored in the storage 72, and the calculated temperature of the inducing member 30.

Third Embodiment

Figure 10:
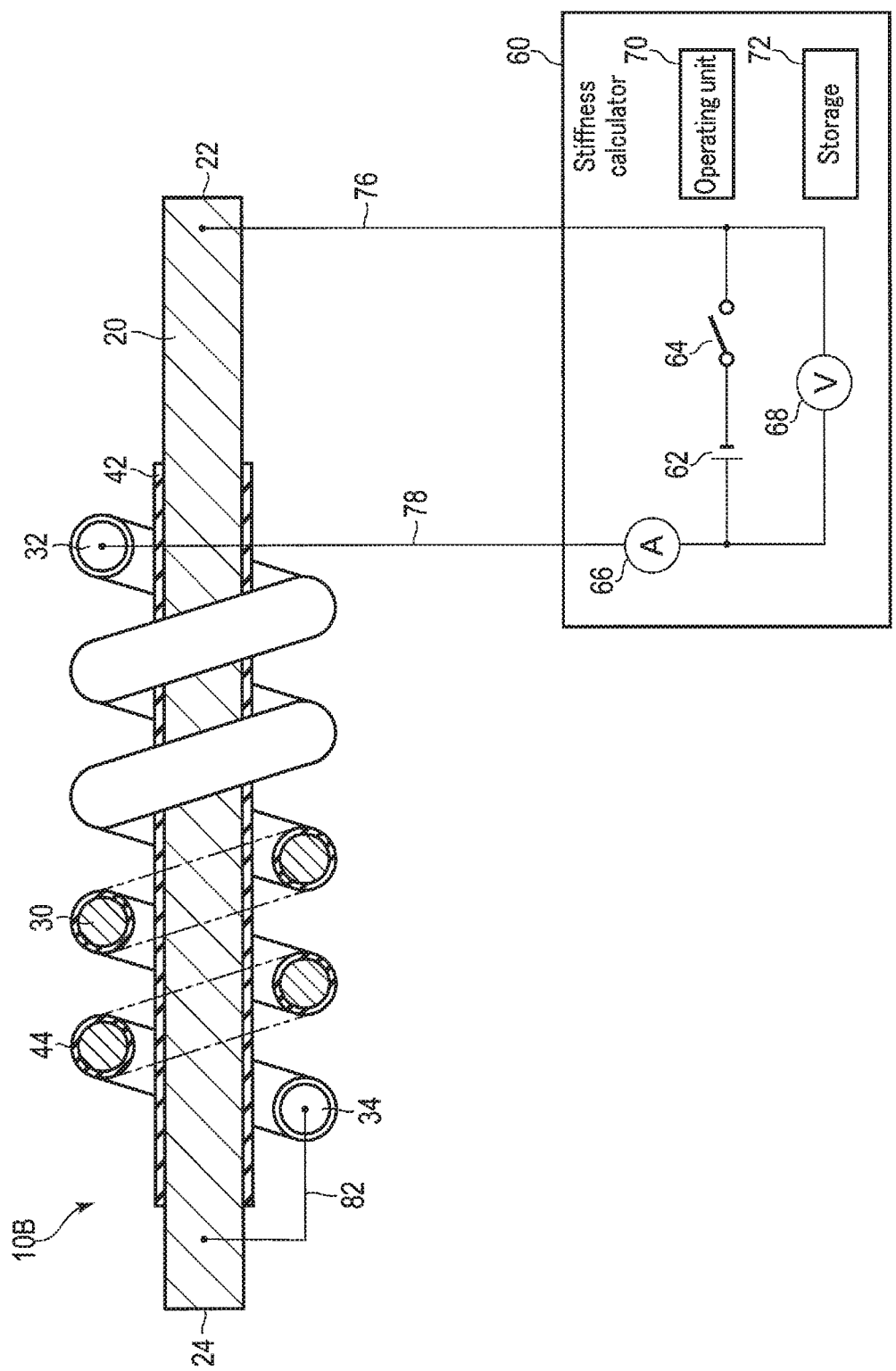
FIG. 10 shows a variable-stiffness actuator according to a third embodiment.

FIG. 10 shows a variable-stiffness actuator according to a third embodiment. In FIG. 10, the members denoted by the same reference numerals as used in FIG. 1 are members similar to those of FIG. 1, and a detailed description of such members will be omitted. Hereinafter, a description will be given mainly of the differences. In other words, the points that will not be mentioned below are similar to those of the aforesaid first embodiment.

In the variable-stiffness actuator 10B of the present embodiment, in comparison with the variable-stiffness actuator 10 of the first embodiment, the controller 50 is omitted. Both the inducing member 30 and the shape-memory member 20 are conductive. The first end 32 of the inducing member 30 is electrically connected to the stiffness calculator 60 through the wire 78. The second end 34 of the inducing member 30 is electrically connected to the shape-memory member 20 through a conductive member 82. The conductive member 82 may be constituted by, for example, a wire, but is not limited thereto. As long as the conductive member 82 is a structural member enabling electrical connection, it may be formed by calking, welding, brazing, soldering, conductive adhesion, or the like. Near the first end 22, the shape-memory member 20 is electrically connected to the stiffness calculator 60 through the wire 76.

The stiffness calculator 60 applies voltage between the shape-memory member 20 and the inducing member 30, causing current to flow through the shape-memory member 20 and the inducing member 30. The current detector 66 measures the value of the current flowing through the shape-memory member 20 and the inducing member 30. The voltage detector 68 measures the value of the voltage applied between the shape-memory member 20 and the inducing member 30. The operating unit 70 calculates the resistance values of the shape-memory member 20 and the inducing member 30, based on the current value obtained by the current detector 66 and the voltage value obtained by the voltage detector 68. The operating unit 70 also calculates the temperature of the shape-memory member 20, based on the calculated resistance values. The storage 72 stores the calculated temperature of the shape-memory member 20 together with the related point of time.

The operating unit 70 further calculates the stiffness of the variable-stiffness actuator 10B, based on the calculated temperature of the shape-memory member 20 and the temperature history of the shape-memory member 20 stored in the storage 72. To be more specific, the operating unit 70 determines whether the temperature rises to the present temperature or lowers to the present temperature, based on the temperature history of the shape-memory member 20. With the result of determination taken into account, the operating unit 70 calculates the stiffness of the variable-stiffness actuator 10B, based on the relationship between the temperature and stiffness of the shape-memory member 20 stored in the storage 72 and the calculated temperature of the shape-memory member 20.

Fourth Embodiment

Figure 11:
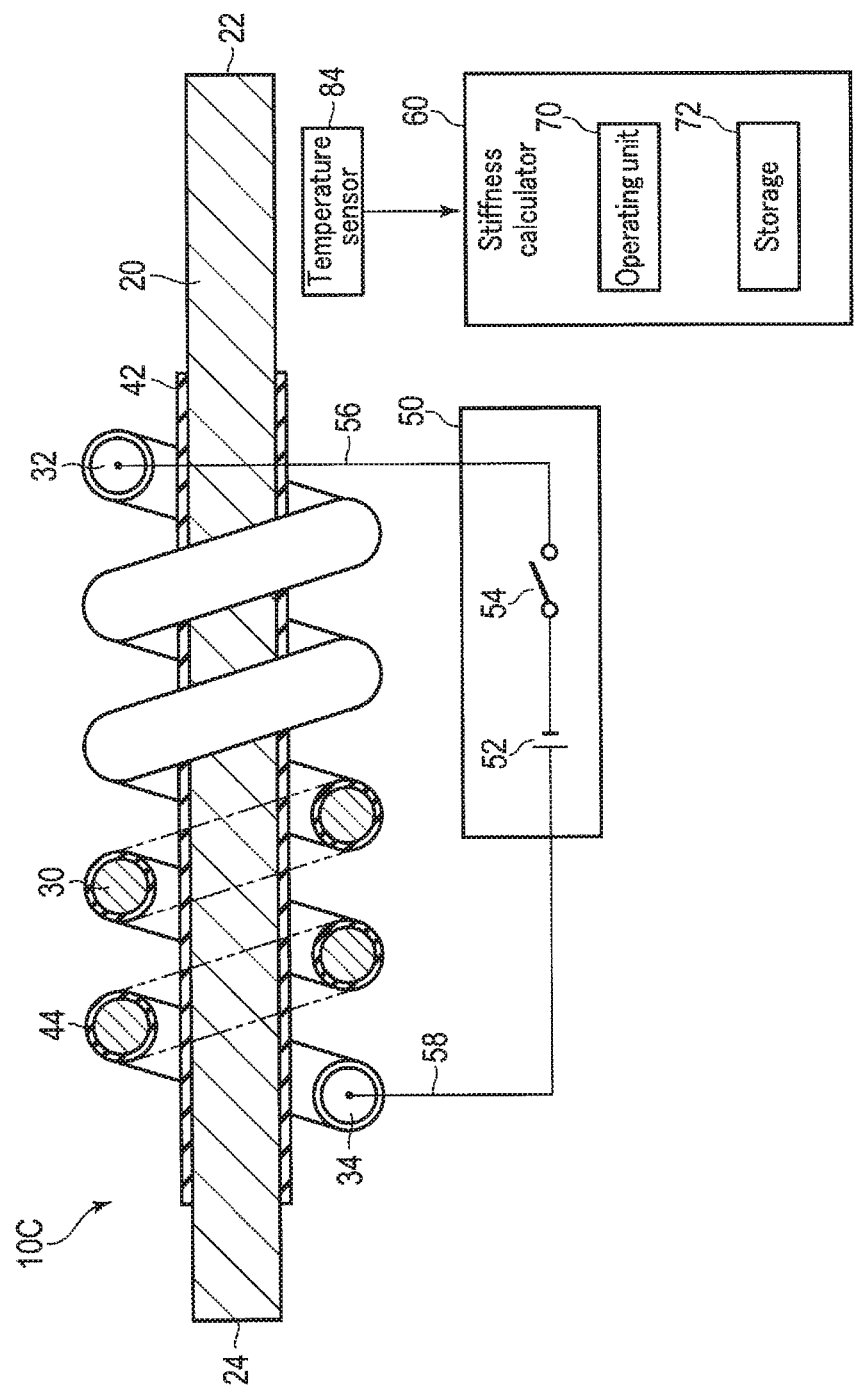
FIG. 11 shows a variable-stiffness actuator according to a fourth embodiment.

FIG. 11 shows a variable-stiffness actuator according to a fourth embodiment. In FIG. 11, the members denoted by the same reference numerals as used in FIG. 1 are members similar to those of FIG. 1, and a detailed description of such members will be omitted. Hereinafter, a description will be given mainly of the differences. In other words, the points that will not be mentioned below are similar to those of the aforesaid first embodiment.

The variable-stiffness actuator 10C further includes a temperature sensor 84 for detecting the temperature of the shape-memory member 20. The temperature sensor 84 is preferably arranged close to that portion of the shape-memory member 20 that is not covered with the insulating film 42.

The controller 50 applies voltage across the inducing member 30, causing current to flow through the inducing member 30. The temperature sensor 84 detects the temperature of the shape-memory member 20 and supplies the detected temperature information to the stiffness calculator 60. The storage 72 stores the temperature information detected by the temperature sensor 84, together with the related point of time.

The operating unit 70 calculates the stiffness of the variable-stiffness actuator 10C, based on the temperature information detected by the temperature sensor 84 and the temperature history of the shape-memory member 20 stored in the storage 72. To be more specific, the operating unit 70 determines whether the temperature rises to the present temperature or lowers to the present temperature, based on the temperature history of the shape-memory member 20. With the result of determination taken into account, the operating unit 70 calculates the stiffness of the variable-stiffness actuator 10C, based on the relationship between the temperature and stiffness of the shape-memory member 20 stored in the storage 72 and the temperature information detected by the temperature sensor 84.

Fifth Embodiment

Figure 12:
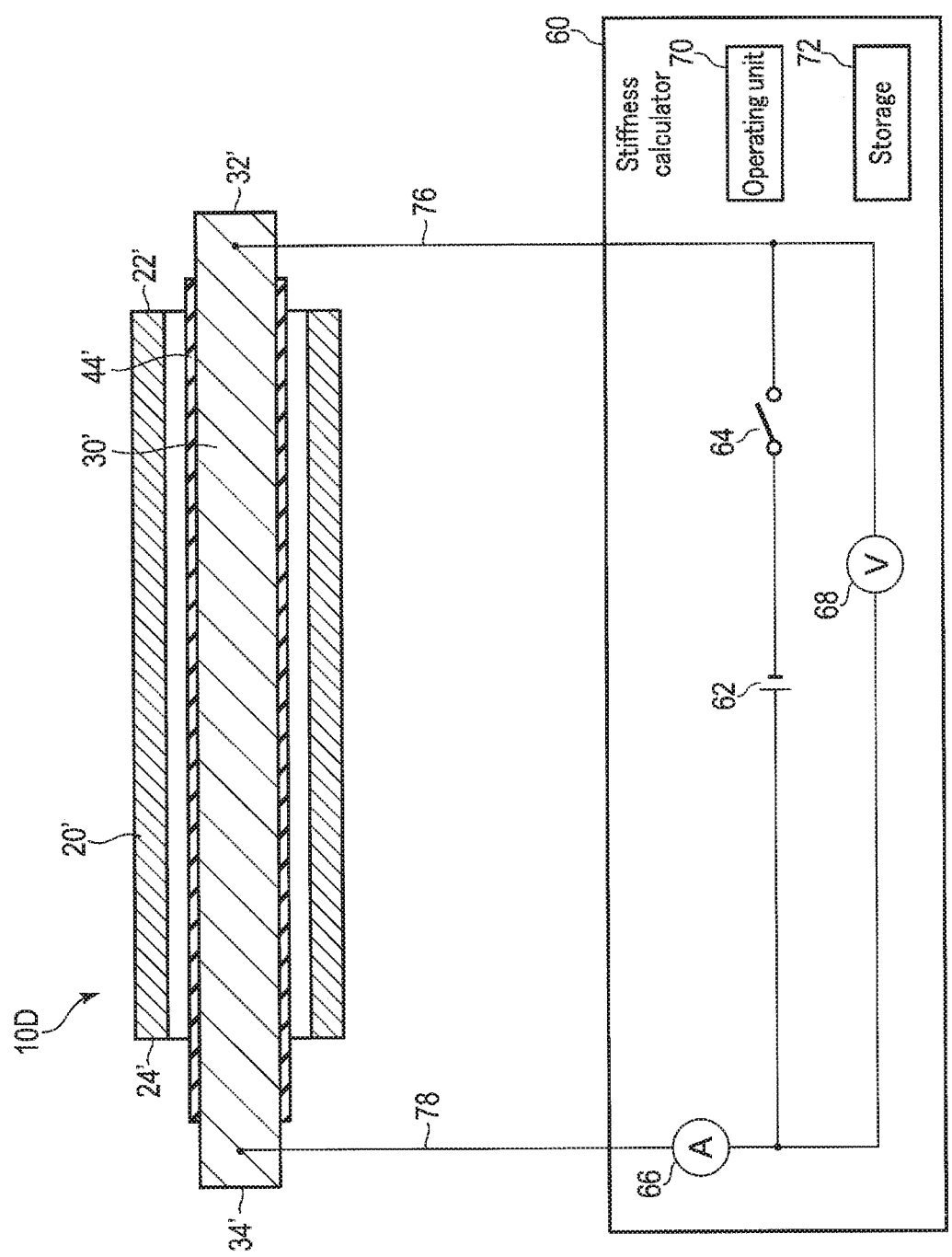
FIG. 12 shows a variable-stiffness actuator according to a fifth embodiment.

FIG. 12 shows a variable-stiffness actuator according to a fifth embodiment. In FIG. 12, the members denoted by the same reference numerals as used in FIG. 1 are members similar to those of FIG. 1, and a detailed description of such members will be omitted. Hereinafter, a description will be given mainly of the differences. In other words, the points that will not be mentioned below are similar to those of the aforesaid first embodiment.

Like the variable-stiffness actuator 10 mentioned above, the variable-stiffness actuator 10D of the present embodiment includes a shape-memory member 20' that can transit in phase between the first phase and the second phase and an inducing member 30' that causes phase transition between the first phase and the second phase into the shape-memory member 20'.

The characteristics of shape-memory member 20' are similar to those of shape-memory member 20. Likewise, the characteristics of inducing member 30' are similar to those of inducing member 30.

The shape-memory member 20' is shaped like a pipe. The inducing member 30' is, but not limited to, for example, an easily deformable wire and extends through the inside of the shape-memory member 20'. With this arrangement, the heat generated from the inducing member 30' is transmitted to the shape-memory member 20' with efficiency. Since the elastic modulus of the shape-memory member 20' depends upon its radial dimension, the pipe-shaped shape-memory member 20' exhibits an elastic modulus that is higher than that of a solid structure under the same volume condition, so as to provide high stiffness.

The shape-memory member 20' has a first end 22' and a second end 24', and the inducing member 30' has a first end 32 located close to the first end 22' of the shape-memory member 20' and a second end 34' located close to the second end 24' of the shape-memory member 20'. The inducing member 30' is conductive, and near the first end 32', the inducing member 30' is electrically connected to the wire 76 that is electrically connected to the stiffness calculator 60. Near the second end 34', the inducing member 30' is electrically connected to the wire 78 that is electrically connected to the stiffness calculator 60.

In the variable-stiffness actuator 10D of the present embodiment, in comparison with the variable-stiffness actuator 10 of the first embodiment, the controller 50 is omitted. Instead, the inducing member 30 is electrically connected to the wire 76 connected to the stiffness calculator 60 near the first end 32', and is electrically connected to the wire 78 connected to the stiffness calculator 60 near the second end 34'. That is, in the present embodiment, the stiffness calculator 60 also has the same function as the controller 50 of the first embodiment.

In the present embodiment, the storage 72 stores the relationship between the temperature of the inducing member 30' and the stiffness of the shape-memory member 20' beforehand, in place of the relationship between the temperature and stiffness of the shape-memory member 20 in the first embodiment. The inducing member 30' is conductive, but the shape-memory member 20' need not be necessarily conductive and may be non-conductive.

The stiffness calculator 60 applies voltage across the inducing member 30', causing current to flow through the inducing member 30'. The current detector 66 measures the value of the current flowing through the inducing member 30'. The voltage detector 68 measures the value of the voltage applied to the inducing member 30'. The operating unit 70 calculates the resistance value of the inducing member 30', based on the current value obtained by the current detector 66 and the voltage value obtained by the voltage detector 68. The operating unit 70 also calculates the temperature of the inducing member 30', based on the calculated resistance value. The storage 72 stores the calculated temperature of the inducing member 30' together with the related point of time.

The operating unit 70 further calculates the stiffness of the variable-stiffness actuator 10D, based on the calculated temperature of the inducing member 30' and the temperature history of the inducing member 30' stored in the storage 72. To be more specific, the operating unit 70 determines whether the temperature rises to the present temperature or lowers to the present temperature, based on the temperature history of the inducing member 30'. With the result of determination taken into account, the operating unit 70 calculates the stiffness of the variable-stiffness actuator 10D, based on the relationship between the temperature of the inducing member 30' and the stiffness of the shape-memory member 20', which is stored in the storage 72, and the calculated temperature of the inducing member 30'.

The variable-stiffness actuator of each of the embodiments described above includes a single inducing member, but may be modified to include inducing members. In this case, the stiffness calculator calculates the temperature each of the inducing members or the temperature of part of the shape-memory member located close to each of the inducing members; alternatively, detects the temperature of part of the shape-memory member located close to each of the inducing members by temperature sensors. Further, the stiffness calculator calculates the stiffness of part of the shape-memory member located close to each of the inducing members, independently. As a result, the temperature distribution or the stiffness distribution of the shape-memory member can be acquired.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A variable-stiffness actuator for use in a flexible member and capable of providing different stiffnesses for the flexible member, the variable-stiffness actuator comprising:
   a shape-memory member that can transit in phase between a first phase and a second phase, the shape-memory member taking a flexible state in which the shape-memory member is easily deformable by an external force when the shape-memory member is in the first phase, so as to provide a first stiffness for the flexible member, the shape-memory member taking a rigid state in which the shape-memory member tends to take a memorized shape memorized beforehand against an external force when the shape-memory member is in the second phase, so as to provide a second stiffness for the flexible member, the second stiffness being greater than the first stiffness;
   an inducing member that causes a phase transition between the first phase and the second phase into the shape-memory member;
   a memory that stores a temperature history of the inducing member;
   a power source;
   a switch connected in series to the power source, the power source and the switch being connected across the inducing member;
   a current detector configured to detect current flowing through the power source and the switch;
   a voltage detector configured to detect voltage applied across a complex of the power source and the switch; and
   a controller for calculating the stiffness of the variable-stiffness actuator,
   the controller calculating the stiffness of the variable-stiffness actuator based on a current temperature of the inducing member and the temperature history of the inducing member stored in the memory;
   wherein the controller calculates the current temperature of the inducing member, based on a resistance value of the inducing member; and
   the controller calculates the resistance value of the inducing member based on information obtained by the current detector and information obtained by the voltage detector.

2. The variable-stiffness actuator according to claim 1, wherein the controller calculates the stiffness of the variable-stiffness actuator, based on a resistance value of the shape-memory member and the resistance value of the inducing member.

3. A variable-stiffness actuator for use in a flexible member and capable of providing different stiffnesses for the flexible member, the variable-stiffness actuator comprising:
   a shape-memory member that can transit in phase between a first phase and a second phase, the shape-memory member taking a flexible state in which the shape-memory member is easily deformable by an external force when the shape-memory member is in the first phase, so as to provide a first stiffness for the flexible member, the shape-memory member taking a rigid state in which the shape-memory member tends to take a memorized shape memorized beforehand against an external force when the shape-memory member is in a second phase, so as to provide a second stiffness for the flexible member, the second stiffness being greater than the first stiffness;
   an inducing member that causes a phase transition between the first phase and the second phase into the shape-memory member;
   a memory that stores a temperature history of the shape memory member;
   a power source;
   a switch connected in series to the power source, the power source and the switch being connected across the inducing member;
   a current detector configured to detect current flowing through the power source and the switch;
   a voltage detector configured to detect voltage applied across a complex of the power source and the switch; and
   a controller for calculating the stiffness of the variable-stiffness actuator,
   wherein the controller calculating the stiffness of the variable-stiffness actuator based on a current temperature of the shape memory member and the temperature history of the shape-memory member stored in the memory;
   the controller calculates the current temperature of the shape-memory member, based on a resistance value of the shape-memory member; and
   the controller calculates a resistance value of the shape memory member based on information obtained by the current detector and information obtained by the voltage detector.

4. A variable-stiffness actuator for use in a flexible member and capable of providing different stiffnesses for the flexible member, the variable-stiffness actuator comprising:
- a shape-memory member that can transit in phase between a first phase and a second phase, the shape-memory member taking a flexible state in which the shape-memory member is easily deformable by an external force when the shape-memory member is in the first phase, so as to provide a first stiffness for the flexible member, the shape-memory member taking a rigid state in which the shape-memory member tends to take a memorized shape memorized beforehand against an external force when the shape-memory member is in the second phase, so as to provide a second stiffness for the flexible member, the second stiffness being greater than the first stiffness;
- an inducing member that causes a phase transition between the first phase and the second phase into the shape-memory member;
- a memory that stores a temperature history of the inducing member; and
- a controller for calculating the stiffness of the variable-stiffness actuator,
- wherein the controller calculates the stiffness of the variable-stiffness actuator based only on a current temperature of the inducing member and the temperature history of the inducing member stored in the memory.

5. A variable-stiffness actuator for use in a flexible member and capable of providing different stiffnesses for the flexible member, the variable-stiffness actuator comprising:
- a shape-memory member that can transit in phase between a first phase and a second phase, the shape-memory member taking a flexible state in which the shape-memory member is easily deformable by an external force when the shape-memory member is in the first phase, so as to provide a first stiffness for the flexible member, the shape-memory member taking a rigid state in which the shape-memory member tends to take a memorized shape memorized beforehand against an external force when the shape-memory member is in the second phase, so as to provide a second stiffness for the flexible member, the second stiffness being greater than the first stiffness;
- an inducing member that causes a phase transition between the first phase and the second phase into the shape-memory member;
- a memory that stores a temperature history of the inducing member; and
- a controller for calculating the stiffness of the variable-stiffness actuator,
- wherein the controller calculates the stiffness of the variable-stiffness actuator based only on a current temperature of the inducing member and the temperature history of the inducing member stored in the memory.

* * * * *